United States Patent [19]

Johnson

[11] Patent Number: 5,002,538

[45] Date of Patent: Mar. 26, 1991

[54] SYRINGE ADAPTER AND METHOD

[76] Inventor: Johnnie M. Johnson, 6655 N. Canyon Crest, #7237, Tucson, Ariz. 85715

[21] Appl. No.: 262,441

[22] Filed: Oct. 25, 1988

[51] Int. Cl.$^5$ ............................................. A61M 5/00
[52] U.S. Cl. ................................................... 604/240
[58] Field of Search ............... 604/191, 192, 240, 241, 604/243, 263, 264

[56] References Cited

U.S. PATENT DOCUMENTS

| | | | |
|---|---|---|---|
| 596,159 | 2/1897 | Haycock | 604/241 |
| 715,290 | 9/1902 | Porter | 604/241 |
| 836,367 | 11/1906 | Detmers | 604/241 |
| 1,231,497 | 6/1917 | Cook | 604/240 |
| 1,604,224 | 7/1925 | Friedman | 604/241 |
| 2,679,246 | 7/1952 | Cohen | 604/263 |
| 2,695,613 | 2/1953 | MacGregor | 604/243 |
| 2,699,777 | 1/1955 | Voorhorst | 128/215 |
| 2,842,126 | 3/1954 | Brown | 604/243 |
| 3,200,486 | 8/1965 | Shields | 604/206 |
| 3,278,357 | 10/1966 | Gettig et al. | 156/294 |
| 3,367,331 | 2/1968 | Brookfield | 604/243 |
| 3,638,650 | 2/1972 | Burke et al. | 128/221 |
| 3,874,383 | 4/1975 | Glowacki | 604/110 |
| 3,976,069 | 8/1976 | Ong | 604/192 |
| 4,232,670 | 11/1980 | Richter et al. | 604/241 |
| 4,334,536 | 6/1982 | Pfleger | 604/263 |
| 4,430,080 | 2/1984 | Pasquini et al. | 604/240 |
| 4,435,176 | 3/1984 | Ishikawa | 604/190 |
| 4,471,765 | 9/1984 | Strauss et al. | 604/191 |
| 4,568,336 | 2/1986 | Cooper | 604/243 |
| 4,675,020 | 6/1987 | McPhee | 604/411 |
| 4,747,835 | 5/1988 | Sandhaus | 604/192 |
| 4,747,839 | 5/1988 | Tarello et al. | 604/240 |
| 4,752,291 | 6/1988 | Magrath | 604/240 |

FOREIGN PATENT DOCUMENTS

| | | | |
|---|---|---|---|
| 0799218 | 11/1968 | Canada | 604/240 |
| 0182531 | 5/1936 | Switzerland | 604/240 |
| 0025678 | of 1903 | United Kingdom | 604/240 |

OTHER PUBLICATIONS

Fournier, *Body Sculpturing Through Syringe Liposuction and Autologsus Fat Re-Injection*, 1987, pp. 5-6, 22-24.
"B-D Kit", Sales Brochure.

Primary Examiner—C. Fred Rosenbaum
Assistant Examiner—Sharon Rose
Attorney, Agent, or Firm—Cahill, Sutton & Thomas

[57] ABSTRACT

An adapter for connecting a cannula to a syringe barrel or a liposuction handle includes a tapered recess that precisely matches a tapered nose of a syringe barrel and a cylindrical recess that precisely matches the cylindrical outside end surface of the syringe barrel. A bore through a nose of the adapter receives the cannula and is in open communication with the tapered recess and the cylindrical recess.

13 Claims, 2 Drawing Sheets

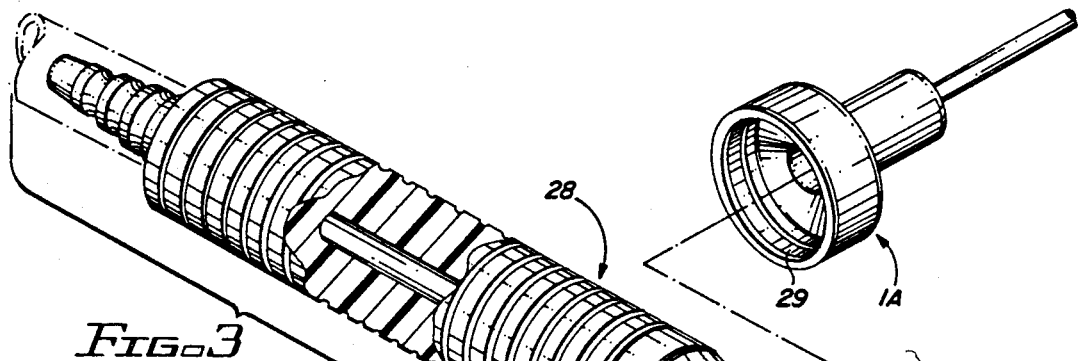
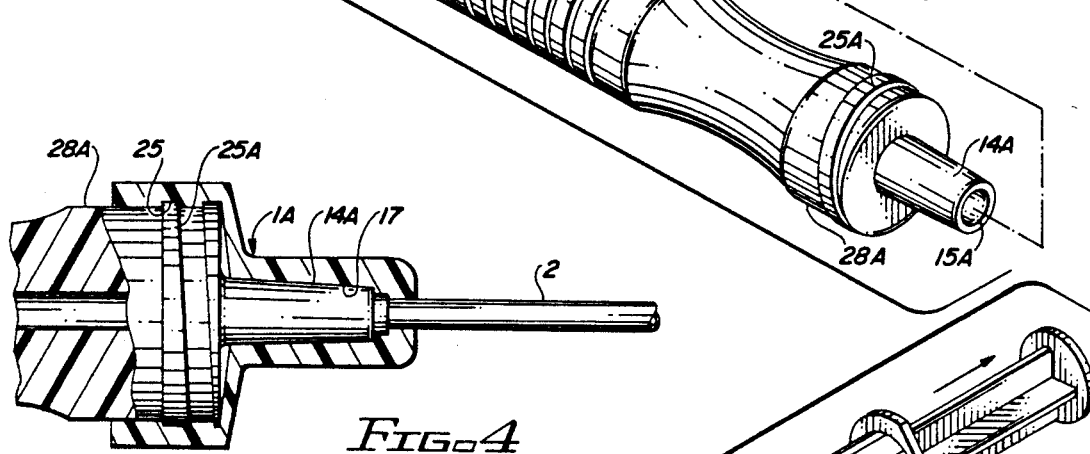
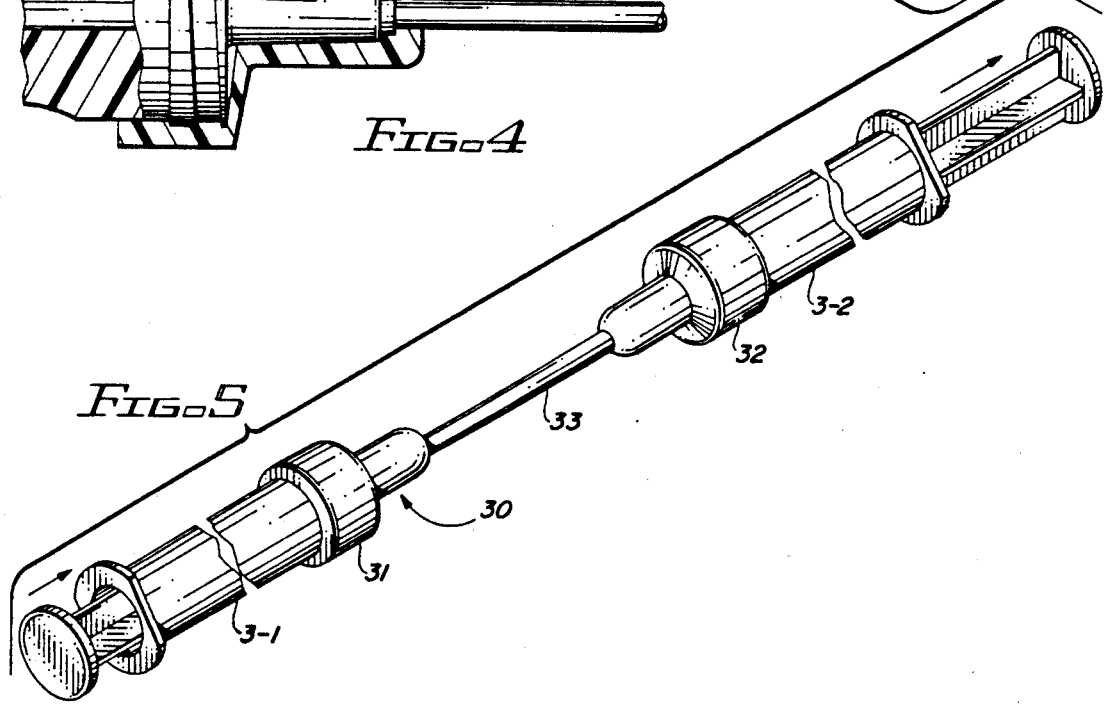

SYRINGE ADAPTER AND METHOD

BACKGROUND OF THE INVENTION

The invention relates to an adapter for supporting cannulas, such as those used for liposuction surgery and needles, and for attaching such a cannula or needle to a plastic syringe barrel with a Luer taper or other tip styles such as toomey, feeding, eccentric, etc.

Many syringes that are in use today for various medical or clinical purposes are designed without a needle permanently attached. In such syringes, the syringe barrel may be tapered at its distal end so that a female connector of a needle assembly may be attached thereto. One widely known connection of this kind is the LUER-LOK connection which allows the needle to be readily attached to the syringe by a twisting movement. The LUER-LOK attachment of a needle to a syringe barrel is advantageous inasmuch as different size needles may be attached to a particular syringe barrel. Other syringe barrels have a tapered nose which is referred to as a Luer taper coupling. The prior syringe needle connecting techniques have an inherent weakness which is a severe disadvantage when large amounts of force, especially forces transverse to the cannula axis, are applied during use of the syringe. During liposuction surgery or during harvesting of bone marrow or the like, surgeons vigorously manipulate a liposuction handle or a syringe barrel to apply large longitudinal transverse, and twisting forces to a cannula in order to loosen fat cells or other cells before they can be suctioned through the cannula. The prior Luer or LUER-LOK connections are subJect to breakage, resulting in exposure of the suctioned cells to air, possibly causing leakage of harvested cells around the syringe adapter connection and contamination thereof by foreign substances present on the outer surface of the syringe, and possibly also causing punctures in surgical gloves during attempts to attach or remove the Luer or slip needles.

In the LUER-LOK connection, the collar expands slightly when a cannula or syringe needle is twisted in the usual fashion to engage the collar. This expansion increases the likelihood of leakage and contamination of liquid being either injected or harvested. There have been instances in which blood being withdrawn by a LUER-LOK syringe has leaked and come in contact with the skin or eyes of attending medical personnel, subjecting them to a possibility of contacting AIDS.

In spite of the popularity of the Luer and LUER-LOK connections, there remains an unmet need for a much more contamination resistant, leakproof, airtight, rigid cannula-to-syringe barrel or cannula-to-liposuction handle adapter having far greater rigidity than previously has been possible.

When harvesting fat cells for manufacture of autologous collagen to be reinjected in the same patient for eliminating wrinkles, it is necessary for the surgeon to be able to control the amount of vacuum in the syringe barrel to avoid damage to harvested fat cells.

There frequently is a need to transfer withdrawn body fluids from a withdrawing syringe into another syringe for reinjection, as many times fluids are withdrawn in a large syringe but reinjection is done with a smaller syringe or syringes. Transfer from one syringe to another may be subject to contamination.

SUMMARY OF THE INVENTION

Accordingly, it is an object of the invention to provide a much more contamination resistant, rigid, leakproof connection supporting a needle or cannula on a syringe barrel or a liposuction handle than has been previously achieved.

It is another object of the invention to provide a device which allows reliable, contamination-free transfer of fluids between syringes.

It is another object of the invention to provide an improved syringe structure that avoids contamination of harvested or suctioned cells.

Briefly described, and in accordance with one embodiment thereof, the invention includes a cannula-to-syringe barrel or cannula to-liposuction handle adapter including both a tapered recess that precisely matches a tapered nose of a syringe barrel and a cylindrical recess that precisely matches the outside distal end surface of the syringe barrel. The adapter has a tip that supports the cannula, and also has an enlarged collar having therein a precision enlarged cylindrical recess or cavity. The collar tightly fits over the distal end of a syringe barrel inserted into the cavity, so that when the adapter is properly seated, the taper of the syringe barrel nose is precisely seated in the tapered recess, and the distal end of the syringe barrel is tightly seated in the enlarged cavity. This connection provides a double seal, the first seal being at the Luer taper of the syringe barrel nose and the other seal being between the circumference of the syringe barrel and the inner surface of the enlarged collar. The dual seal, the largeness of the pressure bearing surfaces, and the large spacing between the centers of force of the pressure bearing surfaces results in a syringe capable of safely withstanding the large longitudinal forces and the large transverse and twisting forces transmitted to a large cannula by a large syringe barrel or a liposuction handle.

In another embodiment of the invention, the inner surface of the enlarged collar can be threaded to mate with threads on a liposuction handle.

In another embodiment of the invention, two adapters are provided on opposite ends of a tube and are mounted on two syringe barrels. Fluid in one syringe barrel is injected through the tube into the other syringe barrel.

BRIEF DESCRIPTION OF THE DRAWINGS

FIG. 3 is an exploded cutaway perspective view showing a threaded adapter similar to the adapter of FIGS. 1 and 2 and a threaded liposuction handle on which the cannula adapter is mounted.

FIG. 4 is a partial section view of the adapter of FIG. 3.

FIG. 5 is a partial perspective view showing a dual-adapter device to allow syringe-to-syringe fluid transfer.

FIG. 6 is a partial section view of the device of FIG. 5.

DETAILED DESCRIPTION OF THE PREFERRED EMBODIMENTS OF THE INVENTION

Figure 1:
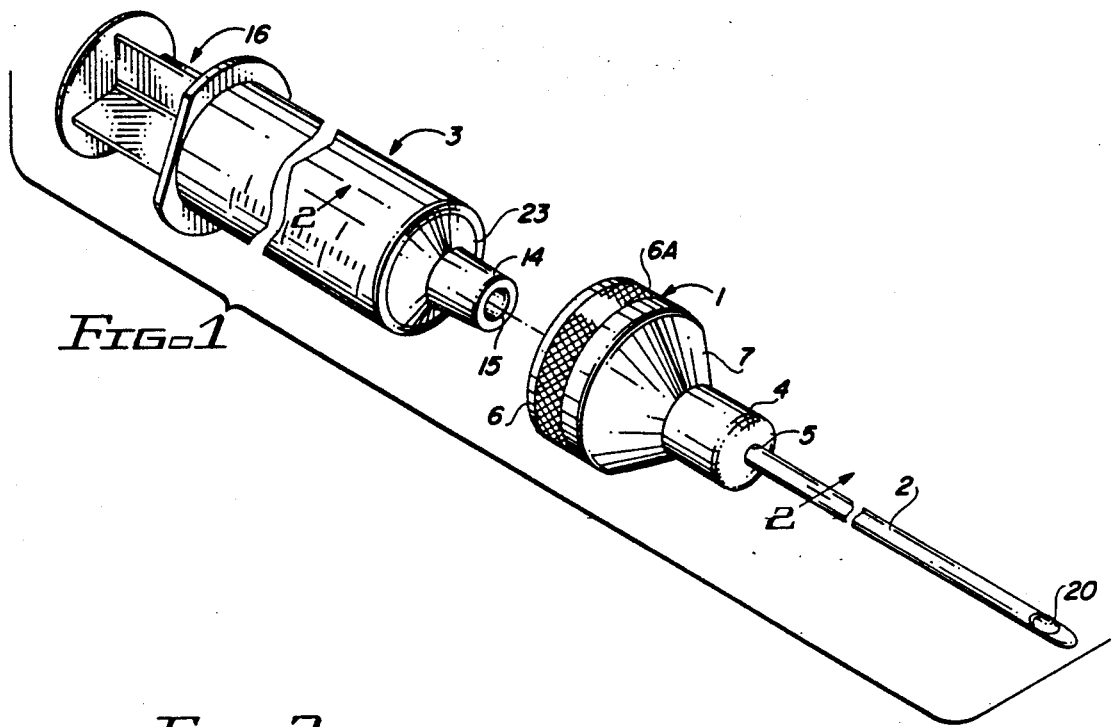
FIG. 1 is a perspective view showing a syringe including a cannula, the cannula adapter of the present invention, and a syringe barrel on which the cannula adapter is mounted.
Figure 2:
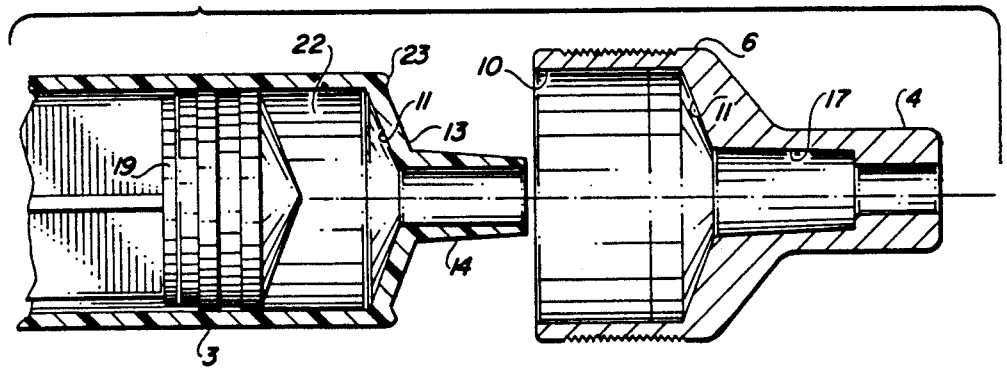
FIG. 2 is a section view taken along section line 2—2 of FIG. 1.
Figure 2A:
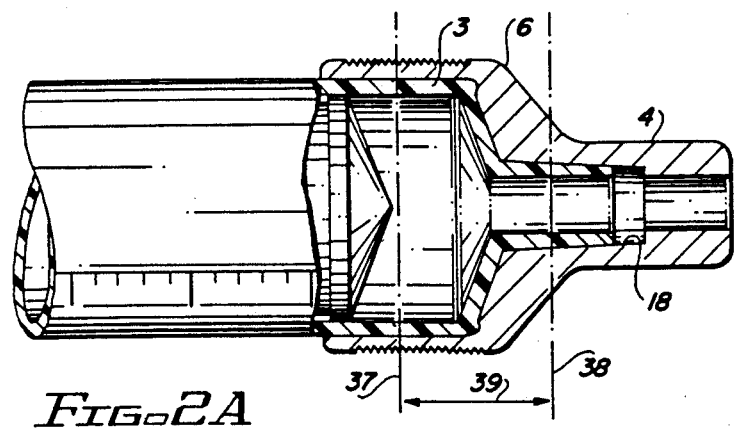
FIG. 2A is a section view similar to section 1 showing the cannula adapter mounted on the syringe barrel.

Referring to FIGS. 1, 2, and 2A, the cannula 2 or needle (which may be a liposuction cannula having a length of approximately 1 to 45 centimeters and a diameter of approximately 21 gauge (i.e. 1/21 of an inch) to 10 mm) has an inlet opening 20 and is attached to a tip 4 of cannula adapter 1. The proximal end of cannula 2 extends from a hole 5 in tip 4, and is sealed thereto by a variety of ways including impact fitting, adhesive, pressure fitting, welding, hypothermia, hyperthermia or injection molding.

The proximal end of tip 4 extends from a tapered shoulder 7, which extends outward to a cylindrical collar 6. Collar 6, if desired, can be knurled as indicated by 6A to provide an improved twist grip thereon.

A syringe barrel 3 having a plunger 16 with a piston 19 thereon moves within a cylindrical cavity 22 of the syringe barrel. Syringe barrel 3 has a tapered nose 14 with a so-called Luer taper thereon. A longitudinal hole 15 extends through nose 14 into the interior of syringe barrel 3. The tapered nose 14 extends axially outward from a tapered shoulder 13 extending from the end of syringe barrel 3.

As shown in FIGS. 2 and 2A, the tip 4 of adapter 1 has a precisely matched mirror image frusto-conical tapered bore 17 therein. The taper slope and the depth of tapered recess 17 precisely match the taper slope and length of the nose 14 of syringe barrel 3. The tolerances of the dimentions of tapered bore 17 are accurate to within ±0.001 inches, to provide an air-tight, non-expandable, liquid-resistant seal when the adapter 1 is tightly mounted on syringe barrel 3.

An enlarged cylindrical bore 10 which is precisely machined to match the diameter of the cylindrical body of syringe barrel 3 is provided in enlarged collar 6 of adapter 1. A tapered shoulder 11 between cylindrical bore 10 and tapered bore 17 may have precisely the same taper slope as the shoulder 13 of syringe barrel 3. Adapter 1 can be made of aluminum, plastics, stainless steel, titanium or the like.

Many syringe barrels of the type indicated by numeral 3 have a lip 23, which typically extends forward approximately 0.002 inches from the cylindrical outer surface of syringe barrel 3. The tolerance between the outer diameter of syringe barrel 3 and the inside diameter of cylindrical bore 10 is 0.001 inches. Thus, when adapter 1 is fully pressed onto syringe barrel 3, as shown in FIG. 2B, very tight seals are formed both between tapered nose 14 and tapered bore 17. Also, another very tight seal is provided between the outer surface of syringe barrel 3 and the surface of cylindrical bore 10.

Further sealing can be provided between lip 23 and a recess in the tapered shoulder 11 at the end of cylindrical bore 10. The lip 23 may further enhance "locking" of adapter 1 to the syringe barrel 3. In operation, twisting of adapter 1 relative to syringe barrel 3 is what causes the lip 23 to more tightly engage, seal and "lock" with an annular outer portion of tapered shoulder 11.

Numeral 14 designates a space between the end of nose 17 and the tapered bore 17. The tolerance for gap 18 is 0.001 inches. There could be a space in gap 18 for a collar of a removeable cannula.

FIGS. 3, 3A, and 4 show a modified version of cannula adapter 25, wherein threads 25 are provided to mate with threads 29 of a typical liposuction handle 28. Liposuction handle 28 also has a tapered nose, designated by reference numeral 14A and precisely mates with the tapered bore 17 of the adapter in the manner described above.

FIG. 5 shows a dual adapter device including two adapters 31 and 32, which are essentially identical to adapter 1 of FIG. 1, attached to opposite ends of cannula-like tube 33. Numeral 3-1 designates a syringe barrel containing fluid and numeral 3-2 designates a receiving syringe barrel. The plunger of syringe barrel 3-1 is depressed, transferring its contents into syringe barrel 3-2 in a completely sanitary manner. The rigid connection of the adapters 31 and 32 prevents any likelihood of breakage or leakage at either of the connections to the syringe barrel or either of the connections to the needle or tube 33.

It can be seen that all of the above described embodiments of the invention provide a great deal of pressure bearing surface area contact between substantially spaced contact points. Dotted line 37 designates the center of force applied between the outside surface of syringe body 3 or the inside surface of cylindrical bore 10. Dotted line 38 designates the center of force applied by tapered bore 17 on tapered nose 14. The distance 39 can be as much as an inch for a large adapter of the type used for a liposuction cannula. A tremendous amount of transverse or twisting force can be applied either to a syringe barrel or a liposuction handle and applied both axially and transversely to the cannula axis without any danger of either breaking the adapter or breaking the seal between the adapter 1 and the liposuction handle or syringe barrel. This configuration clearly overcomes the weaknesses inherent in the prior Luer and LUER-LOK type syringe barrel-to-needle adapter connections.

The term "needle" as used herein may refer to a cannula. The Luer taper referred to in the drawings also can be a LUER-LOK.

While the invention has been described with reference to several particular embodiments thereof, those skilled in the art will be able to make various modifications to the described embodiments of the invention without departing from the true spirit and scope thereof.

What is claimed is:

1. An adapter for rigidly connecting a straight needle to a syringe barrel having a tapered nose extending coaxially with and forward from a distal end of the syringe barrel, the adapter comprising in combination:
   (a) a nose section having an elongated opening for receiving and supporting the straight needle and a tapered recess that matches and contacts the entire the tapered surface of the tapered nose of the syringe barrel to form a seal with the tapered nose;
   (b) an enlarged collar section attached to the nose section and surrounding a cylindrical recess having an inside diameter that is substantially equal to an outside diameter of the syringe barrel, the cylindrical recess being in open communication with the tapered recess and the elongated opening;
   (c) a shoulder connecting the collar section to the nose section, whereby the collar section can be longitudinally slide onto and form a first seal with the syringe barrel and the tapered nose simultaneously slides into and forms a second seal with the tapered recess, a center of force applied between an outer surface of the syringe barrel and an inner surface of the cylindrical recess being substantially spaced from a center of force applied by an inner surface of the tapered recess on an outer surface of the tapered nose to provide a rigid connection of the straight needle to the syringe barrel, which rigid connection withstands substantial transverse force applied by the syringe barrel to the straight needle via the adapter without breaking the first and second seals between the adapter and the syringe barrel.

2. The adapter of claim 1 wherein the cylindrical recess is threaded to mate with a threaded end of a liposuction handle so that the adapter connects the cannula to the liposuction handle.

3. The adapter of claim 1 wherein the collar section has a roughened outer surface to enhance gripping and twisting of the adapter while inserting the tapered nose and a distal end of the syringe barrel into the tapered recess and the cylindrical recess, respectively, of the adapter.

4. The adapter of claim 1 wherein the tapered nose has a Luer-lock.

5. The adapter of claim 1 wherein the syringe barrel is formed of plastic and the adapter is formed of metal.

6. The adapter of claim 1 wherein the syringe barrel is formed of plastic and the adapter is formed of plastic.

7. The adapter of claim 1 wherein the shoulder has a tapered inner surface that accommodates a tapered shoulder of a distal end of the syringe barrel.

8. The adapter of claim 1 wherein the tapered recess is elongated and frusto-conical.

9. A method of connecting a needle to a syringe barrel having a tapered nose attached to a distal end thereof or a liposuction handle having a tapered nose attached to a distal end thereof, the method comprising the steps of:

(a) attaching the needle to a nose section of an adapter, the adapter having an enlarged cylindrical recess, a tapered recess in the nose section in fluid communication with the enlarged cylindrical recess, and a passage in the nose section extending from a distal end of the tapered recess into a passage through the needle;

(b) axially inserting a distal end of the syringe barrel into the cylindrical recess so that the tapered nose of the syringe barrel fits tightly into the forms a first seal with the tapered recess and simultaneously the distal end of the syringe barrel fits tightly into the cylindrical recess and an outer surface of the syringe barrel forms a second seal with the cylindrical recess, a center of force applied between an outer surface of the syringe barrel and an inner surface of the cylindrical recess being substantially spaced from a center of force applied by an inner surface of the tapered recess on an outer surface of the tapered nose o provide a rigid connection of the needle to the syringe barrel, which rigid connection withstands great transverse force applied by the syringe barrel to the needle via the adapter without breaking the first and second seals between he adapter and the syringe barrel.

10. The method of claim 7 wherein step (b) includes twisting the adapter about a longitudinal axis thereof while inserting the distal end of the syringe barrel into the cylindrical recess.

11. The method of claim 10 including continuing to insert the distal end of the syringe barrel until the tapered nose seats tightly in the tapered recess and a forward lip of the distal end of the syringe barrel tightly abuts a bottom of the cylindrical recess.

12. An adapter for rigidly connecting a needle to a liposuction handle having a tapered nose extending coaxially with and forward from a distal end of the liposuction handle, the adapter comprising in combination:

(a) a nose section having an elongated opening for receiving and supporting the needle and a tapered recess that closely mates with essentially all of the tapered surface of the tapered nose of the liposuction handle to form a seal with the tapered nose;

(b) an enlarged collar section attached to the nose section and surrounding a cylindrical recess having an inside diameter that is substantially equal to an outside diameter of the liposuction handle, the cylindrical recess being in open communication with the tapered recess and the elongated opening;

(c) a shoulder connecting the collar section to the nose section, whereby the collar section can be longitudinally slid onto and form a first seal with the liposuction handle and the tapered nose simultaneously slide into and forms a second seal with the tapered recess, a center of force applied between an outer surface of the liposuction handle and an inner surface of the cylindrical recess being substantially spaced from a center of force applied by an inner surface of the tapered recess on an outer surface of the tapered nose to a rigid connection of the needle to the liposuction handle, which rigid connection withstands substantial transverse force applied by the liposuction handle to the needle via the adapter without breaking the first and second seals between the adapter and the liposuction handle.

13. A method of connecting a needle to a liposuction handle having a tapered nose attached to a distal end thereof, the method comprising the steps of:

(a) attaching the needle to a nose section of an adapter, the adapter having an enlarged cylindrical recess, a tapered recess in the nose section in fluid communication with the enlarged cylindrical recess, and a passage in the nose section extending from a distal end of the tapered recess into a passage through the needle;

(b) axially inserting a distal end of the liposuction handle into the cylindrical recess so that the tapered nose of the liposuction handle fits tightly into and forms a first seal with the tapered recess and simultaneously the distal end of the liposuction handle fits tightly into the cylindrical recess and an outer surface of the liposuction handle forms a second seal with the cylindrical recess, a center of force applied between an outer surface of the liposuction handle and an inner surface of the cylindrical recess being substantially spaced from a center of force applied by an inner surface of the tapered recess on an outer surface of the tapered nose to provide a rigid connection of the needle to the liposuction handle, which rigid connection withstands substantial transverse force applied by the liposuction handle to the needle via the adapter without breaking a seal between the adapter and the liposuction handle.

* * * * *